United States Patent [19]

Culver

[11] Patent Number: 4,498,080
[45] Date of Patent: Feb. 5, 1985

[54] APPARATUS AND METHOD FOR TOPOGRAPHIC DISPLAY OF MULTICHANNEL DATA

[75] Inventor: Norman D. Culver, Spotswood, N.J.

[73] Assignee: Braintech, Inc., South Plainfield, N.J.

[21] Appl. No.: 552,502

[22] Filed: Nov. 17, 1983

Related U.S. Application Data

[62] Division of Ser. No. 221,830, Dec. 31, 1980, Pat. No. 4,417,591.

[51] Int. Cl.³ .............................................. G09G 1/02
[52] U.S. Cl. .................................. 340/728; 340/723; 340/734; 340/747; 340/703; 128/730; 128/731
[58] Field of Search ............... 340/728, 725, 723, 734, 340/747, 803, 703; 364/521, 522, 577; 128/731, 732; 367/68

[56] References Cited

U.S. PATENT DOCUMENTS

| | | | |
|---|---|---|---|
| 3,156,110 | 11/1964 | Clynes | 128/660 |
| 3,498,287 | 3/1970 | Ertl . | |
| 3,706,308 | 12/1972 | John et al. . | |
| 3,707,147 | 12/1972 | Sellers . | |
| 3,717,141 | 2/1973 | Krohn et al. . | |
| 3,810,138 | 5/1974 | Thompson et al. | 340/728 |
| 3,841,309 | 10/1974 | Salter et al. . | |
| 3,893,450 | 7/1975 | Ertl . | |
| 4,084,583 | 4/1978 | Hjort | 128/731 |
| 4,094,307 | 6/1978 | Young, Jr. . | |
| 4,171,696 | 10/1979 | John | 128/731 |
| 4,188,956 | 2/1980 | John | 128/731 |
| 4,193,092 | 3/1980 | Stoffel | 340/728 |
| 4,201,224 | 5/1980 | John | 128/731 |
| 4,213,465 | 7/1980 | Renheim | 128/731 |
| 4,214,591 | 7/1981 | Sato et al. | 128/731 |
| 4,216,781 | 8/1980 | John | 128/731 |
| 4,228,529 | 10/1980 | Hsu et al. | 367/68 |
| 4,263,593 | 4/1981 | Dagostino et al. | 340/728 |
| 4,276,570 | 6/1981 | Burson et al. | 340/725 |
| 4,281,663 | 8/1981 | Pringle | 128/689 |

OTHER PUBLICATIONS

Duffy et al., "Dyslexia: Regional Differences in Brain Electrical Activity by Topographic Mapping" *Annals of Neurology,* vol. 7, No. 5, May 1980, pp. 412–420.

Duffy et al., "Brain Electrical Activity Mapping (BEAM): A Method for Extending the Clinical Utility of EEG and Evoked Potential Data", *Annals of Neurology,* vol. 5, No. 4, Apr. 1979, pp. 309–321.

Duffy et al., "Dyslexia: Automated Diagnosis by Computerized Classification of Brain Electrical Activity", *Annals of Neurology,* vol. 7, No. 5, May 1980, pp. 421–428.

Childers, D. G., "Automated Visual Evoked-Response System", *Med. & Biol. Eng. & Comput.,* Jul. 1977, pp. 374–380.

Leseve, N. & A. Remond, "Influence des contrastes sur les responses evoquees visuelles", *Seance Du* 4 *Mars,* 1970, pp. 505–516.

Estrin, T. & R. Uzgalis, "Computerized Display of Spatio-Temporal EEG Patterns", *IEEE Trans. on Bio-Medical Eng.,* vol. BME-16, No. 3, Jul. 1969, pp. 192–196.

(List continued on next page.)

*Primary Examiner*—Gerald L. Brigance
*Attorney, Agent, or Firm*—Hamilton, Brook, Smith & Reynolds

[57] ABSTRACT

In a system for displaying multichannel EEG data, data values received from a matrix of EEG electrodes are stored in a random access memory. Digital values to be displayed are interpolated from the input values by addressing selected ones of the inputs from memory, multiplying those inputs by predetermined coefficients taken from a coefficient memory and summing the products. Each element of the display can be determined in that way within one frame time of the display apparatus. The data can be interpolated in real time for a flicker free display at a rate of over 25 frames per second. By displaying separate values associated with each display element as a distinct color, the dimensionality of the display can be increased. The numeric matrix which underlies the expanded topographic display can be stored digitally and further utilized in further operations and displays.

9 Claims, 7 Drawing Figures

OTHER PUBLICATIONS

Allison, T. et al., "The Scalp Topography of Human Visual Evoked Potentials", *Electroencephalography & Clin. Neuro.*, 1977, 42:185–197.

Matsuoka, S. et al., "The Effect of Dexamethasone on Electroencephalograms in Patients with Brain Tumors", *J. Neurosurg.*, vol. 48, Apr. 1978, pp. 601–608.

Lesevre, N. & A. Remond, "Potentials Evoques Par L'Apparition de Patterns: Effects de la Dimension du Pattern et de la Densite des Contrastes", *Electro. & Clin. Neuro.*, vol. 32, 1972, pp. 593–604.

J. R. Bourne et al., "Topological Characteristics of the Visual Evoked Response in Man", *Electro. & Clin. Neurophysiology*, vol. 30, 1971, pp. 423–436.

G. D. Goff et al., "The Scalp Topography of Human Somatosensory and Auditory Evoked Potentials", *Electro. & Clin. Neurophysiology*, vol. 42, pp. 57–76.

Fuchinoue, T. & K. Sano, "Diagnostic Evaluation of Stationary Potential for Head Injury", Dept. of Neurosurgery, University of Tokyo, Japan, 1975, pp. 945–957.

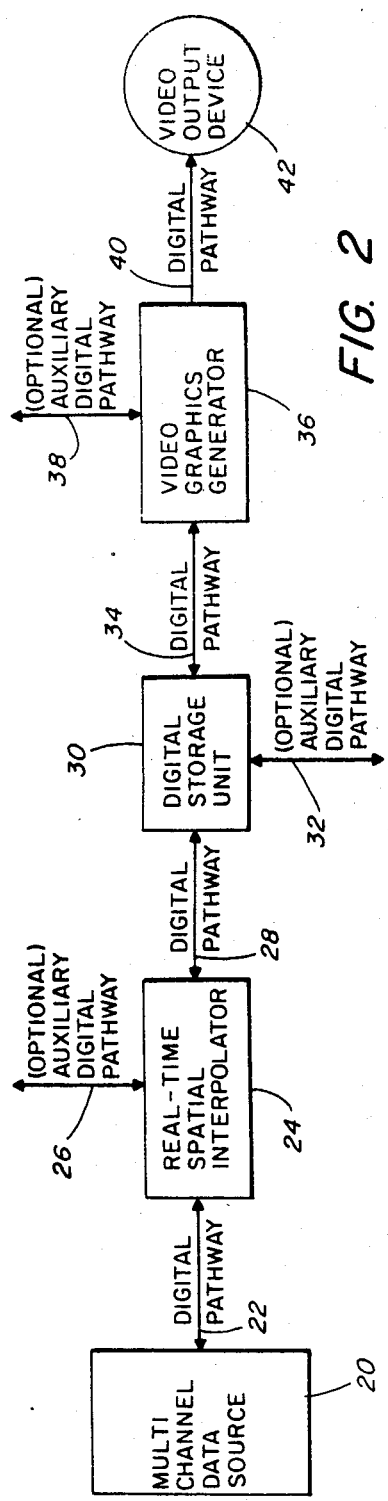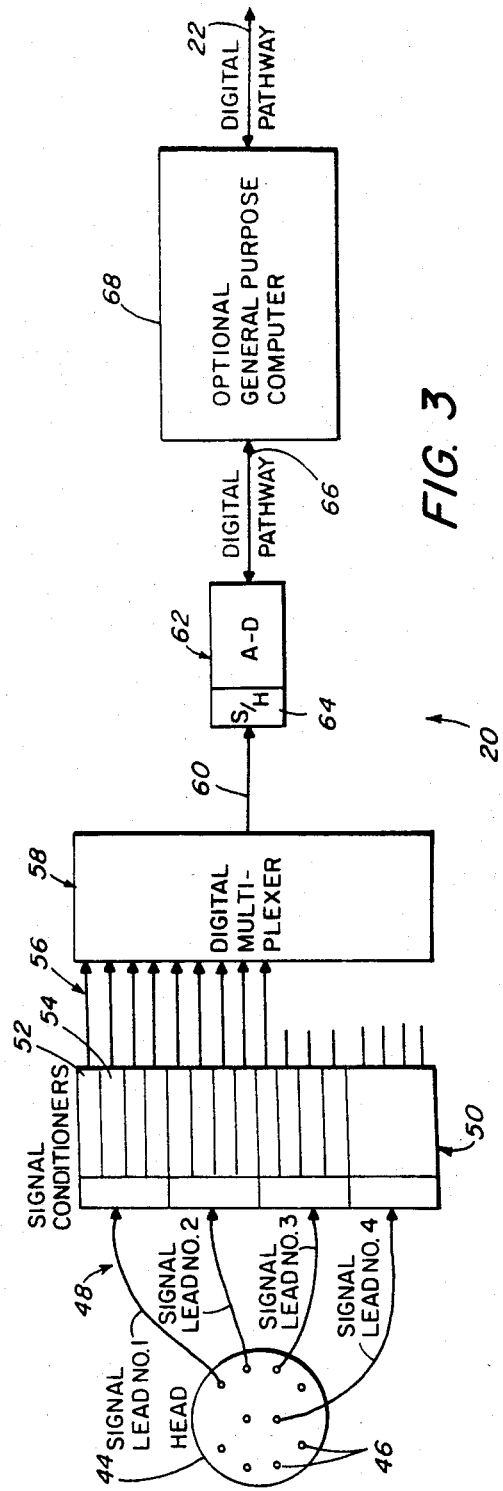

APPARATUS AND METHOD FOR TOPOGRAPHIC DISPLAY OF MULTICHANNEL DATA

RELATED APPLICATIONS

This is a divisional application of U.S. Ser. No. 221,830, filed Dec. 31, 1980, now U.S. Pat. No. 4,417,591.

DESCRIPTION

1. Technical Field

This invention relates to topographic video displays and has particular application to the topographic display of electroencephalographic (EEG) data.

2. Background

Multichannel data poses serious problems for investigators seeking to extract subtle information from a system. A classic example is the analysis of electroencephalographic (EEG) signals produced by the human brain. The volume of data produced by a multi-lead EEG has defied accurate analysis for over 40 years. Another example can be found in the mining industry where geologists search for hints of underlying ore bodies by examining earth samples taken at or near the surface.

In the typical 10–20 EEG system, 20 electrodes are positioned in a matrix on the scalp. The signals are generally analyzed statistically but the information contained in those signals is so voluminous that they are not readily interpreted. More recently, the multichannel information has been output in a topographic video display. By such display, the human eye can be brought to focus on the totality of the data at hand. In a most recent topographic display, based on some of my methods, Duffy et al. have presented a movie-like display of sequential frames of multichannel EEG data in "Brain Electrical Activity Mapping (BEAM): A Method for Extending the Clincal Utility of EEG and Evoked Potential Data," Annals of Neurology, Volume 5, No. 3, April 1979, pp. 309–321. That system makes use of color display and employs interpolation to fill the display around the original electrode signals. With such a motion picture topographic display, the researcher is better able to analyze the EEG data by presenting a more pleasing and rapid display which greatly enhances the investigator's ability to elicit useful information from the data.

An object of this invention is to provide means for rapid display of multichannel data, such as from 20 EEG inputs, which even further enhances the usefulness of such displays in the analysis of data.

A further object of this invention is to provide greater dimensionality to the display than has heretofore been possible with a time sequenced two dimensional display.

SUMMARY OF THE INVENTION

In accordance with my inventive method of utilizing a topographic display to analyze multichannel data, the raw data is expanded as by interpolation to provide a number of display elements an order of magnitude greater than the number of input channels. The thus derived numeric matrix underlying the expanded topographic display is then stored digitally and serves as a source of data for further computational and display operations.

I have further invented an apparatus which facilitates the display in real-time of an arbitrary number of data channels. The display is interpolated so as to provide a smoothly varying topographic representation of the entire space from which the data was sampled. The spatial representation is arbitrary and may or may not reflect an underlying physical reality. The method of interpolation can be varied to suit different assumptions about the way in which information is distributed within the display space.

In a specific embodiment of this invention, data derived from the electrical activity of the brain is displayed. A plurality of EEG electrodes are placed on a patient's skull in a matrix, and the data received from the electrode matrix is expanded in signal processing electronic circuitry to form a larger matrix of display data. In that circuitry, the data from each electrode of the electrode matrix is stored in a random access data memory as an addressable data word. A pointer generator addresses predetermined data words in the data memory for each element of the display matrix. Simultaneously, a coefficient generator provides a predetermined coefficient associated with each data word addressed for each element of the display matrix. The coefficients and addressed data words are combined according to a predetermined function to provide a large matrix of display data signals.

In the preferred interpolating circuitry, the coefficient and pointer generators are random access memories. The coefficients stored in the coefficient RAM are precomputed to provide novel interpolation based on the three data points displayed nearest each display element.

The apparatus also facilitates the coding of up to four dimensions into a single displayable point to increase the dimensionability of the display. The interpolation apparatus is able to independently handle an arbitrary number of dimensions relating to an arbitrary number of input channels. For example, an EEG channel may be preprocessed so as to be represented by several frequency bands instead of a single time varying signal. Each frequency band could be considered to be a "dimension" of the EEG channel. Four dimensional representation is achieved by coding three of the dimensions individually into the red, green and blue components of a color video channel. The fourth dimension is optionally coded into the overall intensity of the unique color so generated. For instance, the "low", "medium" and "high" frequency bands of EEG can be coded as red, green and blue and the RMS voltage can be coded as intensity.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2 is a block diagram of a multichannel topographic display system embodying this invention;

FIG. 3 is a more detailed block diagram of the multichannel data source of FIG. 2 in a system for analyzing EEG signals;

DESCRIPTION OF A PREFERRED EMBODIMENT

Figure 1:
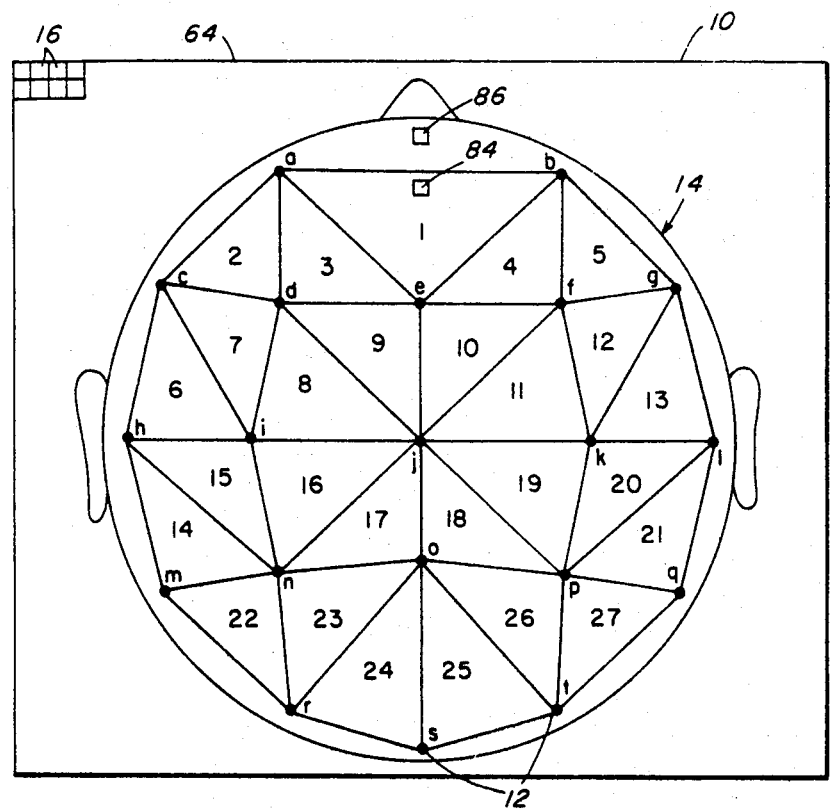
FIG. 1 illustrates a typical electrode matrix oriented with respect to a head outline on a display; also illustrated are segments of the video display, or pixels.

FIG. 1 illustrates the arrangement of electrodes on the scalp of a patient in a typical multichannel EEG test. The electrodes are arranged on the scalp to form a predetermined matrix. As shown in the above-cited Duffy et al. article, the signals received from these electrodes may be used to generate a topographic video display which, in this case, is outlined by the shape of a head 14. A color cathode ray tube has been used to make the display which can be broken into a number of display elements 16 across the entire display screen. The number of elements in the display may be as low as $32 \times 32$ but preferably the display is at least a $64 \times 64$ matrix. It can be seen that even with only a $32 \times 32$ display matrix the number of display segments is an order of magnitude greater than the number of input channels from the electrodes 12. Interpolation is used to fill in the display between the points of the display corresponding to the electrodes. The term interpolation is used loosely to cover such methods as the least squares method for expanding data.

In the system used to make the topographic displays shown in the Duffy et al. article, the data in 24 channels was expanded within each frame by software based interpolation. In that interpolation, the value displayed at each element of a $64 \times 64$ matrix was derived from the values of the three nearest data points. The computation time for each topographic map or frame was under four seconds; thus the 128 maps of usual sequence of maps could be created from the initial 24 input curves in approximately nine minutes. The calculated data was then stored on a disc and later played back from that disc onto a color video display. That display was at a rate of up to ten frames per second.

From the video display, Duffy et al. were able to make decisions for further analysis of the data. Significantly, they were able to rely on the interpolated data as well as the raw data for further information extraction and for further operation on the data. Thus, the raw data was truly expanded, not only for purposes of visual display, but for further statistical and visual analysis of the data. This ability to rely on the underlying numeric matrix, stored in digital form, which underlies the topographic display is a key feature of this invention which makes it a much more significant research and diagnostic tool than has been previously available in topographic displays.

In this novel scientific approach, in which data is expanded to a topographic display and in which that display is used as a jumping off point for further work with the expanded data, it is not necessary for the input data to have a necessary physical relationship to the dimensions of the space in which it is viewed. It is only necessary that the results produce useful data to the eye. Further, regardless of whether the original multichannel data represents a time varying sequence of measurements, I have found that by organizing one dimension of the data into a time varying sequence and thusly displaying the data as a sequence of picture frames greatly enhances the investigator's capability to elicit useful information from the data. Once the data has been arranged in a time varying sequence for a movie-like display, the interpolator discussed below can be used to provide temperal interpolation from frame to frame as well as spatial interpolation within each frame. I have found that by applying a four point Lagrange polynomial across the time sequence of each input channel, I can produce a series of intermediate picture frames which smooth out the perceived transitions from one interpolated picture to the next.

Although the system used to display the Duffy et al. data was the best then available, it did suffer some limitations. For one, the researchers were required to wait at least the nine minutes required for the interpolation computations. Also, due to the limited internal memory in the computer the display data was stored on a memory disc. The display was thus limited by the read time from the disc. It is known in video technology that a frame rate of about 20 frames per second or greater is required to avoid flicker in the display. Thus, at ten frames per second, the cartooned display of Duffey et al. was subject to flicker.

To overcome the above limitations of my previous system, I have developed a real time interpolator for expanding multichannel data, both spatially and temperally, to produce a topographic display. Roughly, real time interpolation means interpolation of the data within about one frame time of the display. Thus, data can be input to the interpolator and the interpolator can produce the new data during the time that a previous frame is being displayed. Thus, the rate of the display is not unduly limited by the interpolation process. To provide a flicker free display, as perceived by the eye, an entire frame should be interpolated at a rate of at least 20 frames per second and preferably at a rate greater than 25 frames per second. A rate of greater than one frame per second will produce flicker but in some applications may be sufficient. Small, low quality displays now generally have a display matrix of about $32 \times 32$ display segments. Preferably, more detailed display matrices such as $64 \times 64$ or greater are used.

The components of a multichannel topographic display system are shown in FIG. 2. A multichannel data source 20 is connected via a digital pathway 22 to a real-time spatial interpolator 24. The interpolator may have an optional auxiliary digital pathway 26 for the purpose of loading pointers and coefficients as will be discussed below. The real-time interpolator transmits its output over a digital pathway 28 to a digital storage unit 30 which in the preferred embodiment is a random access memory. The digital storage unit may have an optional auxiliary digital pathway 32 for the purpose of external insertion and extraction of stored information.

The digital storage unit is accessed via a digital pathway 34 by a video graphics generator 36. The video graphics generator may have an optional auxiliary digital pathway 38 for the purpose of external insertion and extraction of stored information. The video graphics generator transmits its output over an analog pathway 40 to a video output device 42. The digital storage unit 30, the video graphics generator 36, and the video output device 42 are commercially available products.

An example of multichannel data source 20 for EEG is shown in FIG. 3. A head 44 is the original source of micro-volt level signals which are sensed by a multiplicity of electrodes 46. The electrodes are connected via signal leads 48 to signal conditioners 50. Each signal lead may be conditioned by one or more signal conditioning devices 52, 54 which may include amplifiers, filters and so on. The output of the signal conditioners is connected via a pathway 56 to an analog multiplexer 58. The analog multiplexer is capable of being switched so as to present signals in sequence over a single pathway 60 to an analog to digital convertor 62 employing a sample and hold amplifier 64. The output of the a-d convertor is tranmitted over a digital pathway 66. The multichannel data source may optionally contain a general purpose computer 68 which intervenes before the data is finally emitted over digital pathway 22.

Figure 4:
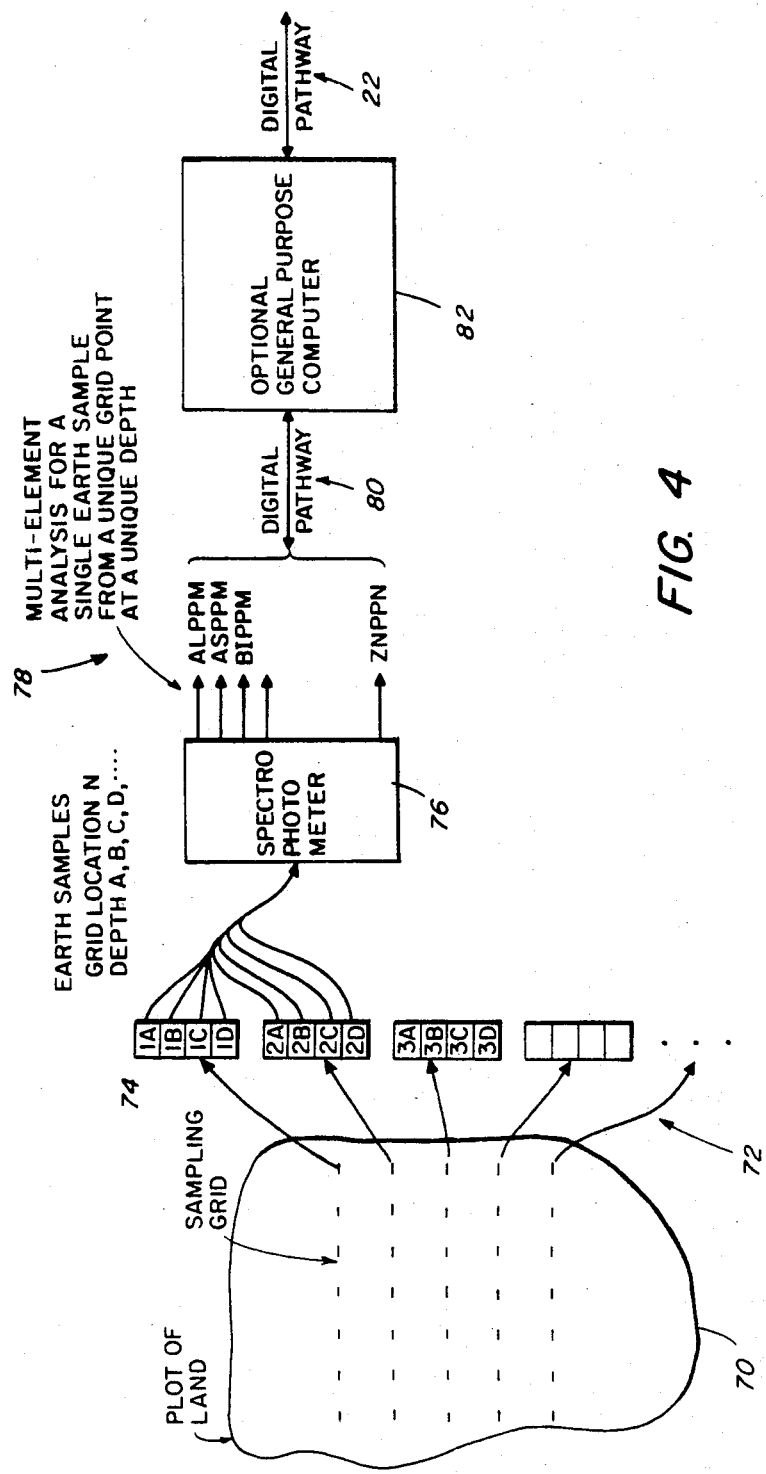
FIG. 4 is an alternative multichannel data source used for analyzing mineral samples.

Another example of a multichannel data source is shown in FIG. 4. In this case the original source of data is a plot of land 70. Earth samples 72 are taken from the land according to a preplanned sampling grid. Each earth sample may consist of a core drilling wherein individual samples 74 for differing depths may be subdivided. Each individual sample is presented to a spectrophotometer 76 which produces a multi-element analysis 78 consisting of measures of the amounts of mineral element present in the samples from each depth of each grid point. The multi-element data is transmitted over a digital pathway 80. An optional general purpose computer 82 may intervene in the output pathway to digital pathway 22.

The real time interpolator 24 serves to expand the raw data to fill in the display. For example the display values in FIG. 1 between the elements 12 associated with the electrodes of an EEG are determined in this circuit.

The interpolated output value Zp for each display element is a linear combination of from 1 to n input values each multiplied by a coefficient.

i.e. $Zp = C1 \times Z1 + C2 \times Z2 + C3 \times Z3 \ldots + Cn \times Zn$

Where:
Z1 is the input value from channel 1.
Z2 is the input value from channel 2.
Z3 is the input value from channel 3.
Zn is the input value from channel n.

For interpolation of EEG signals a triangular interpolation is used. FIG. 1 shows a display screen 10 composed of a grid of pixels 16. Superimposed on the screen is an outline of a head 14. Within the head are 20 input channels 12 arranged so as to represent the 10-20 system of EEG recording. Each input channel 12 is represented in the drawing as a dark dot. A system of triangles is drawn so as to partition the space of the head into regions. Triangular interpolation is the preferred method for EEG interpolation because of the assumed passive resistive character of the skull and overlying skin. Any point lying within the domain of the nearest 3 points which describe a triangle around the point is completely characterized by measuring the voltage at the 3 vertices of the triangle. The pixel 84 lies within the triangle whose vertices are labeled a, e, b. The pixel 86 lies outside any triangle but within the head outline region. The nearest triangle for this pixel is the same triangle labeled a, e, b. Pixels outside the head outline 14 are set to zero.

The interpolation coefficients are calculated as follows: (any X, Y co-ordinate system may be used)

$Ca = (Xp \times (Yb - Ye) + Xb \times (Ye - Yp) + Xe \times (Yp - Yb))/DELTA$ $Cb = (Xa \times (Yp - Ye) + Xp \times (Ye - Ya) + Xe \times (Ya - Yp))/DELTA$ $Ce = (Xa \times (Yb - Yp) + Xb \times (Yp - Ya) + Xp \times (Ya - Yb))/DELTA$ $DELTA = Xa \times (Yb - Ye) + Xb \times (Ye - Ya) + Xe \times (Ya - Yb)$ Where:
Xp is the X co-ordinate of the interpolated point.
Yp is the Y co-ordinate of the interpolated point.
Xa is the X co-ordinate of input channel a.
Ya is the Y co-ordinate of input channel a.
Xb is the X co-ordinate of input channel b.
Yb is the Y co-ordinate of input channel b.
Xe is the X co-ordinate of input channel e.
Ye is the Y co-ordinate of input channel e.

It can be seen that an interpolation can be performed by selecting a value for each display pixel as determined by the above equations. Specifically, for each pixel three data inputs Z must be selected, or pointed out. Each of those inputs is multiplied by a predetermined coefficient C and the resultant products are summed to provide a data value for that display pixel.

It is important to note that the X-Y grid need not be linear. For instance, it could be log-log or it could be defined to represent a square law space. Additionally, the placement of input channels and the outline of the space may be deformed to suit the particular needs of the user.

Figure 5:
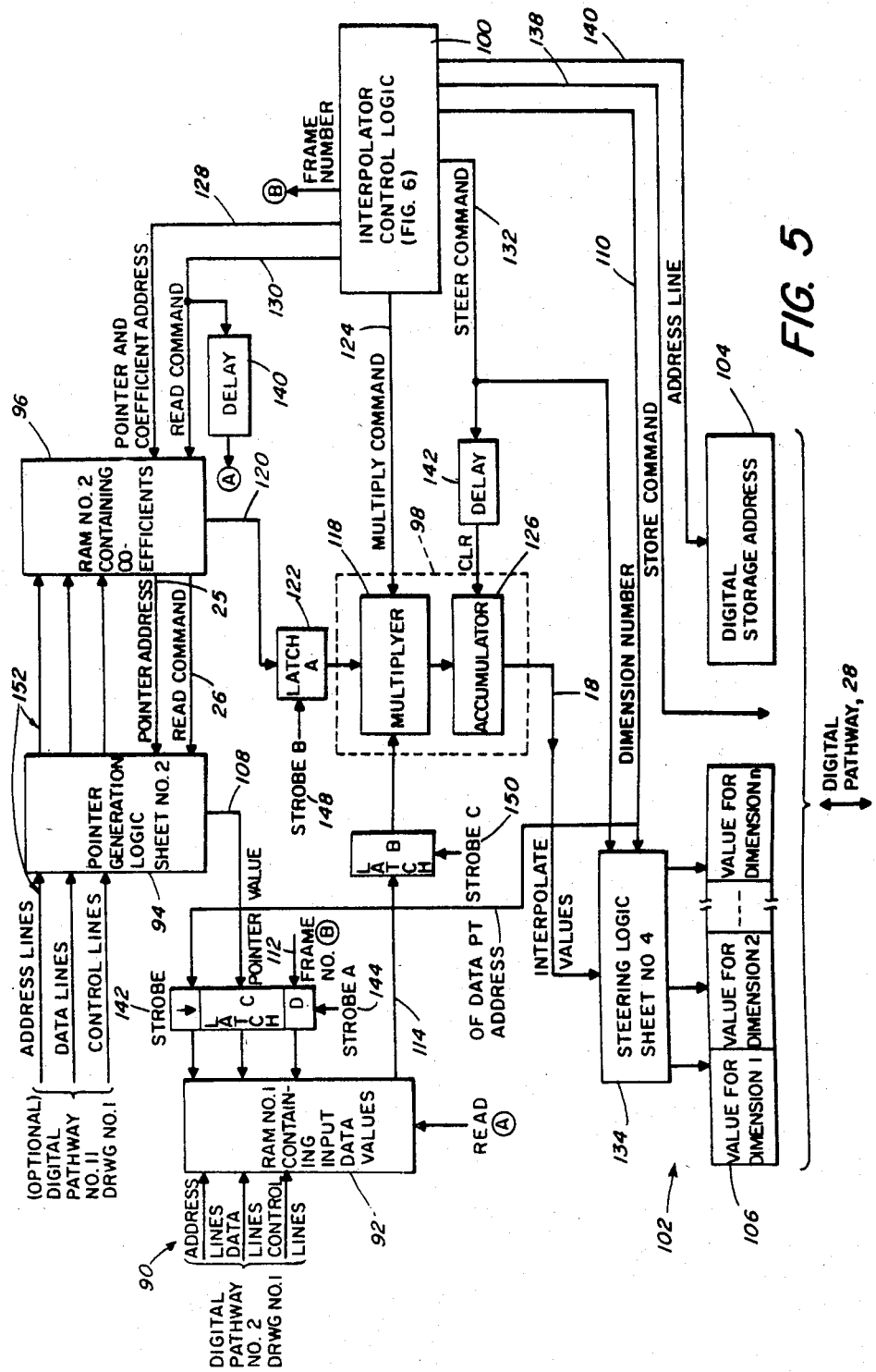
FIG. 5 is a detailed schematic of the real time spatial interpolator of FIG. 2.
Figure 6:
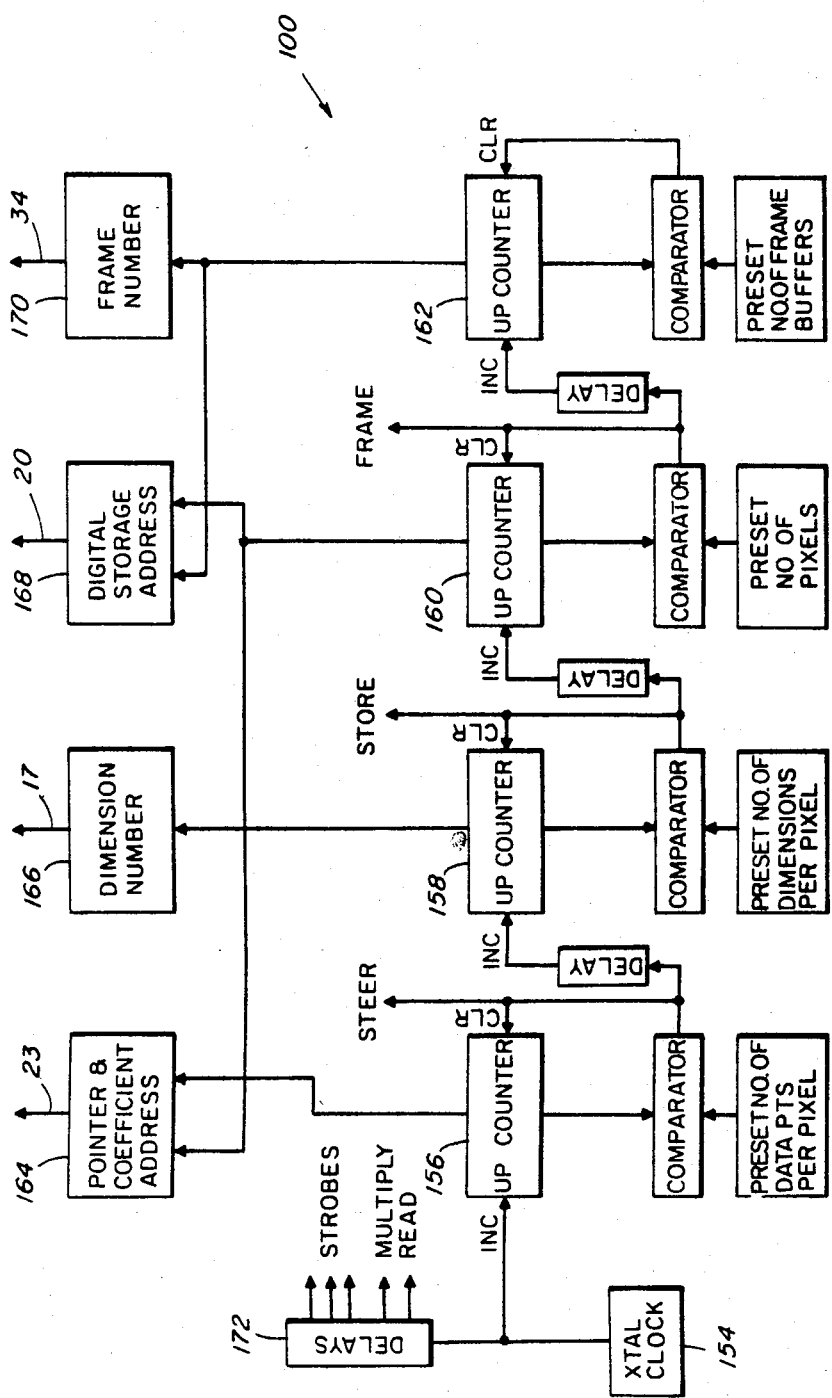
FIG. 6 is a detailed schematic of the control logic for the interpolator circuit of FIG. 5.

The essential elements of my real time interpolator are shown in FIGS. 5 and 6. They comprise an input means 90, an input random access storage means, a pointer and coefficient generator means 94, 96, a multiplier/accumulator means 98, a control means 100 and a steerable output means 102.

The detailed operation of the interpolator is as follows. A set of 12 bit input data values is applied over a digital pathway 90 to a randomly addressable storage array 92. Each of the input data values is assigned a uniquely addressable location in the storage array by suitable coding of the address lines contained in the digital pathway. The further action of the interpolator is to produce a multitude of 8 bit output values based upon the contents of the storage array 92. The output values are applied to digital pathway 28 in a manner such that the digital storage address 104 of each single or multidimensional output value 106 is unique. This manner of operation is effected by control logic 100 of FIG. 6.

Output values 106 are produced using my method of interpolation described earlier, namely each output value is the sum of a number of input data values each multiplied by a suitable coefficient. For each output value a set of pointers and coefficients must be generated so as to effect the sequential action of multiplying and summing.

The pointer generator 94 produces a 6 bit pointer value 108 which acts as part of an address for reading the random access input storage element 92. The entire data value address is composed of a low order two bit part which is supplied by a dimension number 110, a 6 bit middle order part which is supplied by the pointer value 108 and a one bit high order bit supplied by a frame number 112. The approximate data value 114 is applied to a latch 111 whose output is applied to one side of a multiplier 118. The coefficient generator 96 produces a 10 bit coefficient value 120 which is applied to a latch 122 whose output is applied to the other side of the multiplier 118. A multipy command pulse 124 is produced by the control logic 100 and causes the input data value to be multiplied by the coefficient. The result of the multiplication is automatically summed in an accumulator 126. Each multiply and sum step requires the generation of a new pointer and a new coefficient. The control logic 100 produces a pointer and coefficient address 128 for each step. A read command 130 is issued by the control logic to effect the stepwise transition from one set of pointer and coefficients to the next.

Each output value may consist of a single or multidimensioned set of values. An example of a multidimensioned set of values is one which is to be applied to red, green and blue color controls of a video display. Each dimension is computed separately via the interpolation procedure. After the appropriate number of multiply/sum steps is completed for a dimension a steer command pulse 132 is issued by the control logic. The steer command is applied to the steering logic along with the 2 bit dimension number 110 also produced by the control logic. The combination of the steer command pulse and the dimension number causes the steering logic 184 to transmit the contents of the accumulator 126 to the appropriate position in the data value output buffer 106. After an appropriate delay 136 the steer command pulse is used to clear the accumulator prior to the next sequence of multiply/sum steps.

After all the dimension values have been computed and stored in the output buffer 106 the control logic issues a store command 138 and places a suitably unique storage address on the address lines 140.

In order to effect multi-buffered operation or interpolation between frames a frame number 112 is employed to allow more than one picture frames worth of input data to reside in the input scratch pad 92. The frame number consists of one or more bits applied to the high order part of the input storage address. Normally, only one bit is used thus allowing for the simultaneous residence of two frames. The frame number is also coded as the high order bit of the address lines of the input digital pathway 90. The control logic 100 produces the appropriate frame number at the appropriate times.

Harmonious operation is ensured by the use of appropriate delays 140, 142 and timed strobes 144, 146, 148, 150. The strobe pulses are produced by the control logic 100.

The preferred method of implementation for pointer and coefficient generation logic is with semi-conductor random access memories. A digital pathway 152 is to be used to load the RAMs with appropriate values. Alternatively, the appropriate values may be preloaded into ROMs in which case the digital pathway 152 is unnecessary. As another alternative, the pointers and coefficients may be generated by logic circuitry.

FIG. 6 shows the preferred embodiment of the control logic 100. It comprises a clock 154 and four presettable up counters 156, 158, 160 and 162. The outputs of the up counters are mapped into four output busses 164, 166, 168, 170 which contain address-information. As each up counter reaches a preset value, it generates a pulse which is used to clear the up counter, generate a command, and increment the next counter in line after a suitable delay. The clock pulse is also fed to a tappable digital delay line 172 which produces the read, multiply and strobe pulses at suitable times.

Timing of the entire system depends upon the number of output values and number of dimensions being produced. U.S. video rates require that a new frame be presented every 33.3 millesecods. A system which embodies a matrix of 128×128 pixels thus requires that all the dimensions for a pixel be computed and stored within approximately 2 micro-seconds. A three point interpolation for a singled dimensioned pixel requires three multiply/sum steps or approximately 600 nano-seconds per step and a three point interpolation for a four dimensioned pixel requires 12 multiply/sum steps thus allowing approximately 160 nano-seconds per step. Commonly available RAMs such as the 16K 4116-1 made by NEC will access within 120 nano seconds. Statis RAMs such as the 2147 made by National will access within 50 nano seconds. The multiply/sum step is performed by the MPY12 made by TRW within 80 nano seconds. The latched implementation as described above allows the multiply/sum and storage steps to operate in parallel with memory accesses.

The unique characteristics of the color triangle permit multiple dimensions from an input channel to be coded into the red, green and blue outputs of a video generator. This coding permits a singularly unique color to represent a point in a space of three dimensions. If a fourth dimension is coded such that the color remains constant but the intensity changes, the eye can perceive a full four dimensions in the space of a single displayable dot. If the four coded dimensions are independently interpolated, a display screen will accurately depict six dimensions to the human eye.

Figure 7:
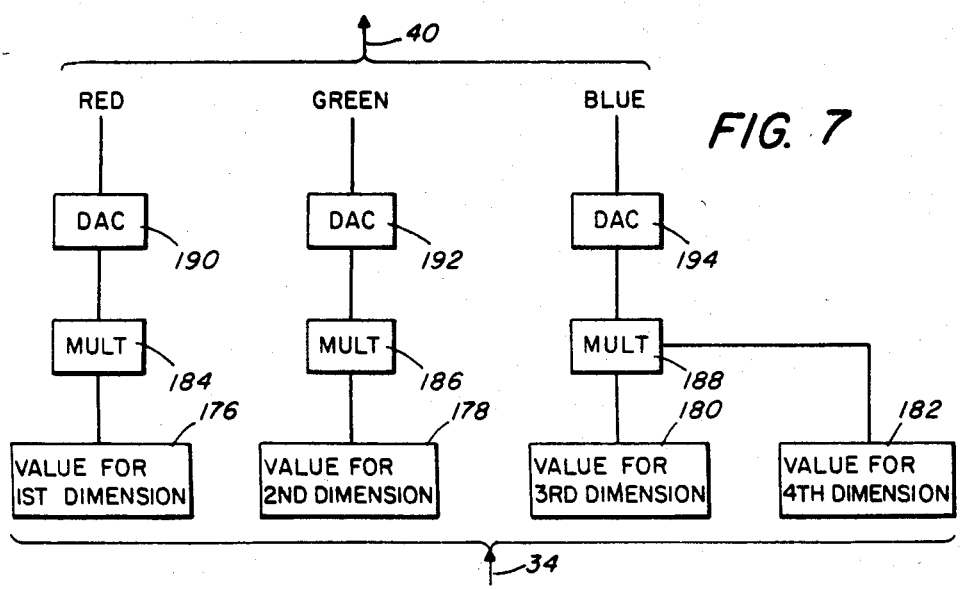
FIG. 7 is a block diagram of a multidimensional color output stage.

FIG. 7 shows the preferred implementation of a multidimensional color output stage. The pixel value is segregated into up to four zones 176, 178 180, 182 of up to eight bits per zone. Each zone represents a single dimension. Three of the zones are applied to the inputs of multipliers 184, 186 188 while the fourth zone is applied to the other input of each of the multipliers. The resultant multipled outputs are applied to the inputs of three Digital to Analog converters 190, 192, 194 which produce individually the analog values corresponding to the Red, Green, and Blue inputs of a commerically available color video monitor.

It may be necessary to individually weight the value of the applied fourth dimensional value for each of the Red, Green, and Blue outputs. This constraint may apply when the color changes as the intensity modulation (fourth dimension) varies. Such weighting depends upon the individual characteristics of color monitors.

Once a set of data has been displayed, hard copy output in the form of photographs is an appropriate archival storage method. Digital storage is perfrered for the numeric matrix underlying the picture.

While the invention has been particularly shown and described with reference to a preferred embodiment thereof, it will be understood by those skilled in the art that various changes in form and details may be made therein without departing from the spirit and scope of the invention as defined by the appended claims.

I claim:

1. A system for displaying data comprising a source of multichannel input data signals derived from a matrix, signal processing electronic circuitry, and a video display for displaying a topographic map of display data, the topographic display comprising a display matrix of a plurality of display elements, the number of display elements being an order of magnitude greater than the number of channels of input data, the signals processing electronic circuitry comprising:
- a digital random access data memory for storing an input data signal from each input channel as an addressable data word;
- a pointer generator for generating a set of addresses of predetermined data words in the data memory for each element of the display matrix;
- data memory access circuitry for receiving the addresses generated by the pointer generator and accessing the predetermined data words;
- a coefficient generator for generaing a predetermined coefficient associated with each data word accessed by the access circuitry; and
- a display data generator for multiplying each accessed data word for each element of the display matrix with its associated coefficient and summing the resultant products to provide a display data signal for that element of the display.

2. A system as claimed in claim 1 wherein the coefficient generator comprises a random access memory in which precalculated coefficients corresponding to input data signals for each element of the display matrix are stored.

3. A system as claimed in claim 2 wherein the pointer generator comprises a random access memory in which predetermined addresses in the data memory are stored, the predetermined addresses in the data memory being those in which input data signals corresponding to each element of the display matrix are stored.

4. A system as claimed in claim 1 wherein the signal processing electronic circuitry comprises means for generating a display data signal $Zp$ for each element of the display matrix from three input data signals $Z1$, $Z2$ and $Z3$ associated with three electrodes, the display of which form a close triangle about said element of the display matrix, and the coefficient generator comprises means for generating coefficients which are a function of the X and Y matrix co-ordinates corresponding to those three input data signals as follows:

$$Zp = (C1 \times Z1) + (C2 \times Z2) + (C3 \times Z3)$$

$$C1 = [Xp\ (Y3-Y3) + X2\ (Y3-Yp) + X3\ (Yp-Y2)]/DELTA$$

$$C2 = [X1\ (Yp-Y3) + Xp\ (Y3-Y1) + X3\ (Y1-Yp)]/DELTA$$

$$C3 = [X1\ (Y2-Yp) + X2\ (Yp-Y1) + Xp\ (Y1-Y2)]/DELTA$$

$$DELTA = X1\ (Y2-Y3) + X2\ (Y3-Y1) + X3\ (Y1-Y2).$$

5. A system as claimed in claim 1 comprising means for generating a multidimensional set of display data signals for each element of the display matrix 6. A system as claimed in claim 5 wherein each display data signal of the set of display data signals is an input display circuitry to control a distinct color at the element of the display matrix.

7. A system for displaying data in a display comprising successive frames of a plurality of display elements, the system comprising a source of multichannel input data signals derived from a matrix and a video display for providing a topographic display, the number of display elements within each frame of the display being an order of magnitude greater than the number of channels of input data, the system further comprising:
- an interpolator circuit for receiving the multichannel input data signals for generating interpolated output data signals, the interpolated output data signal $Zp$ for each display element being generated by the interpolator circuit from three coefficients $C1$, $C2$ and $C3$ and three input data signals $Z1$, $Z2$ and $Z3$ displayed nearest to the generated output data signal, the interpolator circuit comprising coefficient generating means for generating the coefficients as a function of the X and Y matrix co-ordinates of those three input data signals as follows:

$$Zp = (C1 \times Z1) + (C2 \times Z2) + (C3 \times Z3)$$

$$C1 = [Xp\ (Y2-Y3) + X2\ (Y3-Yp) + X3\ (Yp-Y2)]/DELTA$$

$$C2 = [X1\ (Yp-Y3) + Xp\ (Y3-Y1) + X3\ (Y1-Yp)]/DELTA$$

$$C3 = [X1\ (Y2-Yp) + X2\ (Yp-Y1) + Xp\ (Y1-Y2)]/DELTA$$

$$DELTA = X1\ (Y2-Y3) + X2\ (Y3-Y1) + X3\ (Y1-Y2).$$

8. A method of displaying multichannel data at a display rate of at least one frame per second, the number of display elements within an expanded display matrix of each display frame being an order of magnitude greater than the number of channels of input data, the method comprising:
- precomputing, for a particular input matrix of multichannel input data signals and for each individual display element of the expanded display matrix, coefficients for use in generating the expanded display matrix of display signals, and storing the precomputed coefficients in an electronic coefficient memory;
- providing multichannel input data signals;
- storing the multichannel input data signals in an electronic data memory;
- for each display element of the expanded matrix, generating a set of data memory addresses of input data signals;
- accessing the input data signals at the generated addresses;
- electronically generating expanded display data for each display element of the expanded display matrix as a weighted combination of the accessed input data signals and corresponding coefficients stored in the coefficient memory, the expanded display matrix being generated at a rate at least as great as the display rate; and
- displaying the expanded display matrix.

9. A method as claimed in claim 8 wherein the step of generating the expanded display data is at a rate of at least 20 frames per second.

* * * * *